US 6,653,344 B2

(12) United States Patent
Kim et al.

(10) Patent No.: US 6,653,344 B2
(45) Date of Patent: Nov. 25, 2003

(54) PHARMACEUTICAL PREPARATIONS CONTAINING A DIBENZOCYCLOOCTANE LIGNAN DERIVATIVE FOR TREATMENT OF NEURODEGENERATIVE DISEASE

(75) Inventors: Young-Joong Kim, Seoul (KR); Sang-Hyun Sung, Seoul (KR); Mi-Gyeong Lee, Seoul (KR); So-Ra Kim, Seoul (KR); Gyeong-A Gu, Seoul (KR); Won-Ju Jeong, Seoul (KR)

(73) Assignee: Elcom Bio Technology Co., Ltd. (KR)

( * ) Notice: Subject to any disclaimer, the term of this patent is extended or adjusted under 35 U.S.C. 154(b) by 0 days.

(21) Appl. No.: 10/168,394

(22) PCT Filed: Oct. 19, 2001

(86) PCT No.: PCT/KR01/01765
§ 371 (c)(1),
(2), (4) Date: Jun. 19, 2002

(87) PCT Pub. No.: WO02/32417
PCT Pub. Date: Apr. 25, 2002

(65) Prior Publication Data
US 2003/0050335 A1 Mar. 13, 2003

(30) Foreign Application Priority Data
Oct. 19, 2000 (KR) .......................... 200/61676

(51) Int. Cl.⁷ .................. A61K 31/335; A61K 31/34; C07D 317/70; C07C 43/18
(52) U.S. Cl. .................. 514/463; 514/471; 549/432; 568/666
(58) Field of Search .................. 514/463, 471; 549/432; 568/666

(56) References Cited

PUBLICATIONS

Chemical Abstracts vol. 89 No. 24193, Liu et al , Studies on the constituents fo Hua–Zong–Wu–Wei–Zi and related compounds (1976).*

* cited by examiner

Primary Examiner—Alan L. Rotman
Assistant Examiner—Raymond Covington
(74) Attorney, Agent, or Firm—Edwards & Angell, LLP; Peter F. Corless; Christine C. O'Day

(57) ABSTRACT

The present invention relates to the use of a dibenzocyclooctane lignan derivative of the following general formula (I) for treatment of neurodegenerative disorders:

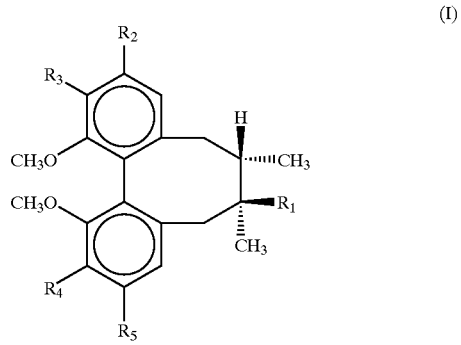

wherein $R_1$ is H or $C_{1-4}$ lower alkyl; $R_2$, $R_3$, $R_4$ and $R_5$ are respectively H, OH, $C_{1-4}$ lower alkyl, $C_{1-4}$ lower alkoxy, or $R_2$ and $R_3$ or $R_4$ and $R_5$ are respectively combined to form the group of —$OCH_2O$—. Pharmaceutical preparations containing the dibenzocyclooctane lignan derivative as the active ingredient also are disclosed.

5 Claims, No Drawings

PHARMACEUTICAL PREPARATIONS CONTAINING A DIBENZOCYCLOOCTANE LIGNAN DERIVATIVE FOR TREATMENT OF NEURODEGENERATIVE DISEASE

TECHNICAL FIELD

The present invention relates to the use of a dibenzocyclooctane lignan derivative of the following general formula (I) for prevention and treatment of neurodegenerative disorders and pharmaceutical preparations containing the same as active ingredient.

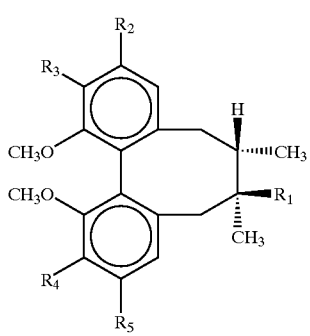

(I)

wherein $R_1$ is H or $C_{1-4}$ lower alkyl, $R_2$, $R_3$, $R_4$ and $R_5$ is respectively H, OH, $C_{1-4}$ lower alkyl, $C_{1-4}$ lower alkoxy, or $R_2$ and $R_3$ or $R_4$ and $R_5$ are respectively combined to form the group of —$OCH_2O$—.

Among the compound of the above formula (I), the compound in which $R_1$ is H, $R_2$ $R_3$, $R_4$ and $R_5$ is deoxyshizandrin: compound 1), the compound in which $R_1$ is H, $R_2$ and $R_3$ are combined to form the group of —$OCH_2O$—, and $R_4$ and $R_5$ are each methoxy is gomisin N: compound 2), and the compound in which $R_1$ is H, and $R_2$ and $R_3$, and $R_4$ and $R_5$ are each combined to form the group of —$OCH_2O$— is wuweizisu C: compound 3).

The above ingredients are known compounds which are contained in *Schizandra chinensis*

BACKGROUND OF THE TECHNOLOGY

The population distribution of the present society changes rapidly to venerable ages. Accordingly, invasion rate of neurodegenerative disorder in relation to venerable ages such as stroke or arthymia is increasing. The death rate for nervy craniales disease is annually increasing. When the death etiology of our country is analysed, the death rate for the nervy craniales disease is the second following to cancer. The world death rate of nervy craniales disease is 2–3rd. However, any drug or treatment method for the diseases has not been suggested until now. The social and economical loss is gradually increasing. The neurodegenerative disease can occur by neurodegeneration caused by concussion of the brain and aging, 2nd phenomena like circulatory disorders and neurodegenerative disorders caused by various physical or mechanical factors like traffic accident, workman's accident, CO-poisoning. (Rothman S M, Trhrston J H and Hauhart R E (1987) Delayed neurotoxicity of excitatory amino acids in vitro. Neuroscience 22: 1884–1891; and Weiloch, T. (1985) Hypoglycemia-induced neuronal damage prevented by NMDA antagonists. Science 230: 681–683).

When brain tissue is damaged, it leads to brain nervous cell-death. The mechanism of nervous cell-death is classified into two distinctive forms. The one is by glutamate existing in central excitatory neurotransmission material. Glutamate in normal state acts as neurotransmission material. When it is excessively secreted, it leads to nervous cell-death. Such neurotoxicity caused by glutamate is classified into acute and chronic forms of response. (Choi D W (1988) Glutamate neurotoxicity and disease of the nervous system. Neuron 1: 623–634). Acute neurotoxicity appears to be mediated by the entry of Na and K into neurons resulting in cell swelling which leads to cell death. In delayed toxicity, N-methyl-D-aspartate, the receptor of glutamate is activated and Ca is flowed into cell and Ca dependent enzyme is over-activated and leads to cell death. (Rothman S M, Thurston J H and Hauhart R E (1987) Delayed neurotoxicity of excitatory amino acids in vitro. Neuroscience 22: 1884–1891; Strijbos P J L M, Leach M J and Garthwaite J (1996) Vicious cycle involving Na+channels, glutamate release and NMDA receptors mediates delayed neurodegeneration through nitric oxide formation. J. Neurosci. 16: 5004–5013; and Coyle J T and Purrfarcken P (1993) Oxidative stress, glutamate and neurodegenerative disorders. Science 262: 689–695).

Second is injury by direct oxidative stress. In the brain, contents of unsaturated fatty acid and consumption of oxygen is high. The formation of oxygen radical is high and the content of antioxidative enzyme is relatively low. The danger of injury caused by free radical including oxygen radical is very high. A study for neurocell death mechanism in relation to neurodegenerative disorders is carried out actively worldwide.

TECHNICAL SUBJECT TO BE ACCOMPLISHED BY THE INVENTION

Preliminary studies in our laboratory indicated that a methanolic extract of dried Schizandra fruit (*S. chinensis*) attenuated neurotoxicity in primary cultures of rat cortical cells induced by L-glutamate. Thus, we attempted to isolate the active constituents of the methanolic extract of the fruits. In the present study, we report that five lignans were obtained from this fruit and identified as deoxyschizandrin, gomisin A, gomisin N, schizandrin and wuweizisu C, respectively. We also report that deoxyschizandrin, gomisin N and wuweizisu C exhibited neuroprotective activities against glutamate-induced neurotoxicity in primary cultures of rat cortical cells. Since early times in orient, Schizandra fruit (*S. chinensis*) have been used as a tonic and in order to protect the liver and have compounds of dibenzocyclooctane lignam. Various studies were carried out for the activity of the compounds. (Nakajima K, Taguchi H, Ikeya Y, Endo Y and Yosioka I (1983) The constituents of Schizandra chinensis Baill. XIII. Quantitative analysis of lignans in the fruits of *Schizandra chinensis* Baill. by high performance liquid chromatography. Yakugaku Zasshi 103: 743–749; Liu G T (1985) In: Advances in Chinese medical materials research (Chang H M et al. Eds) pp.257–268, World Scientific Publishing Co. Singapore). The important activities of dibenzocy clooctane lignan are liver-protecting activity (Hikino H, Kiso Y, Taguchi H and Ikeya Y (1984) Antihepatotoxic actions of lignoids from Schizandra chinensis Fruits. Planta Med. 50: 213–218; Kiso Y, Tohkin M, Hikino H, Ikeya Y and Taguchi H (1985) Mechanism of antihepatotoxic activity of wuweizisu C and gomisin A. Planta Med. 51: 331–334; and Yamada S, Murawaki Y and Kawasaki H (1993) Preventive effect of gomisin A, a lignan component of Schizandra fruits, on acetaminophen-induced hepatotoxicity in rats. Biochem. Pharmacol. 46: 1081–1085), anticancer activity (Yasukawa K, Ikeya Y, Mitsuhashi, Iwasaki M, Abursda M, Nakagawa S, Takeuchi M and Takido M (1992)

Gomisin A inhibits tumor promotion by 12-o-tetra-decanoylphorbol-13-acetate in two-stage carcinogenesis in mouse skin. Oncology 49: 68–71), antiinflamation activity (Wang J P, Raung S L, Hsu M F and Chen C C (1994) Inhibitory by gomisin C (a lignan from *Schizandra chinensis*) of the respiratory burst of rat neutrophils. Brit. J. Pharmacol. 113: 945–953), antiviral activity (Fujihashi T, Hara H, Sakata T, Mori K, Higuchi H, Tanaka A, Kaji H and Kaji A (1995) Anti-human immunodeficiency virus (HIV) activities of halogenated gomisin J derivatives, new non-nucleotide inhibitors of HIV type 1 reverse transcriptase. Antimicrob. Agents Chemother. 39:2000–2007). However, no report appeared that those compounds have phycological activity in neurosystem.

We investigated the neuro-protective activity and mechanims of the dibenzocyclooctane lignan, the important ingredients of Schizandra fruit and ascertained that the dibenzocyclooctane lignan have neuroprotective activity and therefore, the compound can be used as a drug for prevent and treatment of neurodegenerative disorders such as stroke or Alzheimer's disease.

CONSTITUTION OF THE INVENTION

The present invention is more in detail by the following example and experiments.

EXAMPLE

Preparation of Dibenzocyclooctane Lignan

Dried *S. chinensis* fruit was extracted with 80% methanol and the extract was concentrated to obtain total extracts. The total methanol extracts were suspensed in distilled water and extracted with n-hexane to obtain n-hexane fraction. The n-hexane fraction was chromatographed on silicagel column (solvent:hexane:ethyl acetate=100:1~50:1~10:1) to obtain fractions. Each isolated compounds were investigated and identified by spectrophotometric method such as MS, $^1$H-NMR and $^{13}$C-NMR to obtain compound s 1, 2 and 3.

Other dibenzocyclooctane lignan compounds used in the present invention can easily be prepared by known method (Chem. Pham. Bull. 28(8) 2414–2421(1980); Chem. Pharm. Bull. 27(6), 1383–1394(1979).

Experimental Example

Experimental Method

1. Animal:

The Sprague-Dawley mice obtained from the breeding ground of Seoul National University were breeded at the breeding ground of College of Pharmacy, Seoul National University. The breeding ground was maintained 22±5° C. Lightening was performed at from 7 AM to 7 PM. Feed is used solid feed contained crude protain 23.2%, crude lipid 4.0%, crude fiber 6.0%, crude ash 10.0%, crude calcium 0.6% and crude P 0.4% (Seoul, Samyangsa).

2. Cortical Cell Culture

Primary cultures of mixed cortical cells containing both neuron and glia were prepared from fetal rats as described previously (Kim Y C, Kim S R, Markelonis G J and Oh T H (1998) Ginsenosides Rb1 and Rg3 protect cultured rat cortical cells from glutamate-induced neurodegeneration. J. Neurosci. Res. 53: 426–432).

The cortical cells were plated onto collagen-coated dishes at a density of 1×10$^6$ cells/ml. The cultured cells were grown in DMEM supplemented with 10% heat-inactivated fetal calf serum, 1 mM sodium pyruvate, 100 IU/ml pecicillin and 100 μg/ml streptomycin at 37° C. in a humidified atmosphere of 95% air/5% $CO_2$. cultures were allowed to mature for 2 weeks before being used for experiments.

3. Dose of Chemicals

The lignan compounds to be investigated for having neuroprotective activity or not were dissolved in DMSO (within final culture concentration, 0.1%) and diluted with distilled water and by passing the solution through Milli-poremembrane (0.22 μm, Millex-GV, USA) to make sterile state. The solution was cultured, by differentiating the concentration and dosed to neuron cells.

4. Inducement of Neurotoxicity by Glutamate

Cortical cells directly isolated from mouse fetal were cultured for 14 days. The samples to be tested were treated at different concentrations to cultured cells. After one hour, neurotoxicity was induced by treating 100 μM of glutamate. After 24 hours, the survival cell rate were measured by MTT assay to determine neuroprotective activity of the samples.

5. MTT Measurements

To culture broth of the cortical cells during being cultured, MTT(5 mg/ml) was added by 10% of the culture broth. The broth was cultured for more 3 hours. The formed formazan was dissolved by DMSO and was assayed absorption at 540 nm ((Mosmann T (1983) Rapid colorimetric assay for cellular growth and survival: Application to proliferation and cytotoxicity assays. J. Immuno. Methods 65: 55–61)

6. Measurement of $Ca^{2+}$ Concentration in Cells $Ca^{2+}$ concentration of first cultured cortical cells was assayed by dosing samples to be tested and after one hour, neurotoxicity was induced by glutamate and tested by using Fura-2 AM (Grynkiewicz G, Poenie M and Tsien R Y (1985) A new generation of calcium indicators with greatly improved fluorescence properties. J. Biol. Chem. 260: 3440–3450).

7. Measurement of Nitrite

The content of nitrite isolated into culture broth from first cultured cortical cells was assayed by using Griess reagent by Dawson's method (Dawson V L, Brahbhatt H P, Mong J A and Dawson T M (1994) Expression of inducible nitric oxide synthase causes delayed neurotoxicity in primary neuronal-glial cortical cultures. Neuropharmacology 33: 1425–1430).

8. Preparation of Cell Supernatant of Cells

Cells were collected by adding 0.1M potassium phosphate buffer (pH 7.4) to culture-broth-removed remainings from first cultured cortical cells. The collected cells were treated by supersonic wave for 20 seconds and were centrifuged at 4° C. with 3,000 g for 20 minutes to obtain the supernatant.

9. Measurement of Glutathione Peroxidase Activity (GSH-px)

1 ml solution in test tube comprising 100 mM potassium phosphate buffer (pH 7.4), 1 mM reduced glutathione (GSH), 0.2 mM NADPH, 0.5 mM $H_2O_2$ and 1.5 units/ml of GSSG-reductase (GSSG-r) was prepared and 10 μl of cell supernatant was added and reacted. The loss of adsoption at 340 nm was assayed and the activity of GSH-px was measured. The activity of GSH-px was showed as μmol NADPH oxidized/mg protein/min by using absorption coefficient (6.22 μmol cm) (Flohe L, Gunzler W A, 1984, Assays of glutathone peroxidase, Methods Enzymol 105: 114–121).

10. Measurement of Total GSH (GSH+GSSG)

In test tube, 70 μl solution containing 0.3 mM NADPH and 5 mM DTNB was prepared 0.100 μl of cell supernatant was added and final content 5 units/ml of GSSG-R was added thereto and was reacted. The increase of adsoption was measured at 412 nm for 1 minute. The content of GSH was converted and obtained by comparing the content of GSH with GSH standard. (Tietze F, Enzymatic method for quantative determination of nanogram amounts of total and oxidized glutathione, Anal Biochem 27: 502–522).

11. Measurement of Malondialdehyde (MDA) Content

To 500 μl of cell supernatant, 500 μl of 10% trichroroacetic acid(TCA) was added and leaved for 10 minutes. The precipitated protain was removed by using centrifuge. To the supernatant, final concentration of 0.2% of thiobarbituric acid is added to prepare 1 ml of solution and reacted at 100° C. for 1 hour. Adsorption was measured at 535 nm and converted and obtained by comparing the contents of MDA with 1,1,3,3-tetraethoxypropane as standard. (Yagi K A, 1976, Simple fluorometric assay for lipoperoxide in blood plasma, Biochem Med 15: 212–216).

12. Statistical Analysis

The study for statistical significance carried out with number 3 (n=3) for each test groups. Data were evaluated for statistical significance using analysis variance (ANOVA test) The confidence level for statistical significance was set at a probability value of 5%.

13. Results and Discussion

Deoxychizandrin, gomisin N, schizandrin and wuweizisu C, the important dibenzocyclooctane lignans of Schizandra fruit were evaluated by assessing the viability of cultured cortical neurons after treatment with the neurotoxicant, glutamate. The results were showed in Table 1. After cortical cells were cultured for 14 days, test compounds were dosed at different concentrations and after 1 hour neurotoxicity was induced by 100 μM glutamate. After culturing for 24 hours, the neuroprotective activity was measured. The neuroprotective activity of the compounds were measured by MTT assay for assaying the activity of succinate dehydrogenase. When cells were poisoned, mitochondrias in cells were injured and the activity of succinate dehydrogenase existing in mitochondrias was also decreased. And the content of formazan is decreased, too. By using this phenomena, cell survival rate can be measured. By measuring neuroprotective activity, the compounds of the general formula (I) have significant neuroprotective activity. When dosing 1 μM concentration, deoxyschzandrin, gomisin N and wuwiewisu C have the most significant neuroprotective activity and maintained respectively 46.2%, 51.3% and 63.9% level of neurons compared with normal state.

We investigated the protective mechanisms of deoxyschizandrin, gomisin N and wuweizisu C in an attempt to determine at which stage these lignans protected neurons from glutamate-induced toxicity. Cultures were pretreated with the lignans for 24 hours in exposure to glutamate(pre-treatment). In addition, some cultures were exposed to glutamate in DMEM for 24 hours in the absence of lignans (post-treatment). The results showed in the Table 2.

Wuweizisu C was neuroprotective against glutamate-induced toxicity in the case of pre-treatment but not post-treatment. This suggests that this lignan acts on the early state of glutamate toxicity. But, deoxyschizandrin have significant neuroprotective activity, when it is not pre-treated but post-treated. In addition, Gomisin N maintained its activity when it is both pre-treated and post-treated. Accordingly, based upon the above results, deoxyschizandrin, gomisin N and wuweizisu C have respectively, according to different mechanisms, neuroprotective activities against glutamate. Therefore, wuweizisu C is regarded to have neuroprotective activity at the first stage of inducing neurotoxicity by glutamate. Deoxyschizandrin is regarded to have neuroprotective activity, according to a series of reactions, after over-manifest of glutamate-receiptor. In addition, gomisin N is regarded to have all neuroprotective activities which wuweizisu C and deoxyschizandrin have.

Glutamate receptor is divided into NMDA receptor which is activated by NMDA and non-NMDA receptor which is activated by alpha-amino-3-hydroxy-5-methyl-4-isoxazole and kainic acid (KA). To first cultured cortical cells, the above compounds were each treated. The neuroprotective activities of the compounds were measured, after toxicities were induced by NMDA, the NMDA receptor agonist, or KA, the non-NMDA receptor agonist. As a result, wuweizisu C has neuroprotective activity against toxicity induced by NMDA. Deoxyschizandrin has selectively neuroprotective activity against toxicity induced by KA. In addition, gomisin N has relatively better neuroprotective activity against toxicity induced by NMDA, rather than toxicity induced by KA. However, it is confirmed that the selectivity is inferior to deoxyschizandrin or wuweizisu C. The results were shown in the Table 3.

It is known that the neurotoxicity by glutamate is mediated by influx of $Ca^{2+}$ induced by overmanifest of glutamate receptor. This brings in increase of content of $Ca^{2+}$, accumulations of free radical and NO. (Peter et al, 1995; Kriegistein, 1997). $Ca^{2+}$ in cells does a important role for signal transfer and role of cell. Accordingly, homeostasis of $Ca^{2+}$ is systemically regulated. The breakdown of homeostasis of $Ca^{2+}$ induces death of cell and is origins of various illnesses. One of the origin of breakdown of homeostasis of neurons is the increase of $Ca^{2+}$ in cells by glutamate. In case the glutamate receptor is activated, $Ca^{2+}$ is influxed into cells and the increase of $Ca^{2+}$ brings in activations of nitric oxide snythase: NOS), protain kinase C, phospholipase and protease, the $Ca^{2+}$-dependant enzymes. (Choi, 1985: Lipton and Rosenberg 1994). In case such enzymes are activated, various toxicities develop based on a series of reactions.

Therefore, the effects of $Ca^{2+}$ influx by glutamate according to deoxyschizandrin, gomisin N and wuweizisu C were investigated. Gomisin N and wuweizisu C reduced significantly $Ca^{2+}$ concentration influxed into cells. When gomisin N and wuweizisu C were treated each with the 1 μM concentration, those reduced 50.3% and 67.9% of $Ca^{2+}$ contents in cells increased by glutamate. But, deoxyshcizandrin did not significantly effect on $Ca^{2+}$ influx. The results were shown in Table 4.

As stated above, the increase of $Ca^{2+}$ contents in cell by glutamate activates $Ca^{2+}$-dependent enzymes. Activation of NOS, one of Ca dependent enzymes increases formation of NO and appears toxicity. This is one of toxicity mechanisms of glutamate. (Masanori et al, 1998). In case phospholipase A2 is activated, arachidonic acid is formed. Therefore, various free radicals are formed during the metabolism of the arachidonic acid. It is known that oxidative stress is another toxic mechanism of glutamate. Nervous system has various antioxidant mechanisms against oxidative stress. Typical antioxidant mechanism is antioxidant enzymes such as glutathione peroxidase, superoxidedismutase and catalase and glutathione, the typical antioxidant material.

In case glutamate is treated to first cultured cortical cells of mice, formation of NO is increased. Gomisin N and wuweizisu C significantly decrease the contents of NO which is excess-formed by glutamate. When treated with 1 μM concentration, those decreased 60.2% and 65.8% compared with normal state. When schizandrin is treated at the 1 μM concentration, it decreased NO content increased by glutamate. But, the effect is 40.2% level compared with normal state and the effecr is inferior to gomisin N and wuweizisu C. The results were shown in Table 5. When deoxyschizandrin, gomisin N and wuweizisu C are treated at 1 uM concentration to first cultured cortical cells toxicity-induced by glutamate, those maintained about 50% of normal state activity of GSH-px and glutathione decreased by glutamate and have protective activity on the activity of antioxidant enzymes. The results were shown in the Table 6 and 7.

NO which is over-formed by glutamate and superoxide anion are each combined to form peroxynitrite. (Almeida et al. 1998). Such formed peroxynitrite with free radical which is formed by glutamate toxicity induce oxidative stress on neurons and induce lipid-peroxidation of cells. Wuweizusu C suppressed 67% of lipid-peroxidation induced by glutamate. Gomisin N and deoxyschizandrin significantly suppressed lipid-peroxidation induced by glutamate. The results were shown in Table 8.

From the above experimental results, deoxyschizandrin, gomisin N and wuweizisu C significantly have protective activity against neurotoxicity induced by glutamate.

From the above experimental results, the present invention first revealed that wuweizisu C, deoxyschizandrin and gomisin N, the 3 kinds of lignans of *Schizandra chinensis* fruit have protective activities of cortical cells by use of first cultured cortical cells of mice and mechanisms thereof.

TABLE 1

Effects of deoxyschizandrin, gomisin N, and wuweizisu C on cell viability in glutamate-damaged primary cultured rat cortical cells.

|  | Concentration ($\mu$M) | Viability (%) |
|---|---|---|
| Control |  | 100.0 ± 1.4 |
| Glutamate-treated |  | 0.0 ± 6.4 |
| Deoxyschizandrin | 0.1 | 11.6 ± 5.1 |
|  | 1.0 | 46.2 ± 6.3** |
|  | 5.0 | 45.6 ± 3.1** |
| Gomisin N | 0.1 | 25.2 ± 4.4 |
|  | 1.0 | 51.3 ± 8.3** |
|  | 5.0 | 49.2 ± 9.5** |
| Wuweizisu C | 0.1 | 30.2 ± 6.3* |
|  | 1.0 | 63.9 ± 5.9*** |
|  | 5.0 | 60.9 ± 9.6*** |

Rat Cortical cultures were treated with compounds for 1 hr before exposure to 100 M glutamate and then maintained for 24 hr. Cell viability was measured by the MTT assay. Optical density (OD) of the control and glutamate-treated were 1.18±0.09 and 0.75±0.07, respectively. Viability was calculated as 100×(OD of glutamate+compound-treated−OD of glutamate-treated)/(OD of control−OD of glutamate-treated). Values given represent the mean SD (n=3). Mean value is significantly different from the value for the glutamate-treated; $*p<0.05$, $p<0.01$, $*p<0.001$

TABLE 2

Effects of deoxyschizandrin, gomisin N and wuweizisu C on cell viability in glutamate-damaged primary cultured rat cortical cells in pre-treatment.

|  | Viability (%) | |
|---|---|---|
|  | Pre-treatment | Post-treatment |
| Control | 100.0 ± 1.5 | 100.0 ± 2.1 |
| Glutamate-treated | 0.0 ± 5.9 | 0.0 ± 4.7 |
| Deoxyschizandrin | 20.1 ± 3.1 | 45.9 ± 5.5** |
| Gomisin N | 45.5 ± 9.8** | 39.6 ± 6.2* |
| Wuweizisu C | 59.6 ± 5.1*** | 19.2 ± 7.8 |

Rat cortical cultures were treated with compounds at the concentration of 1 M for 1 hr before exposure to 100 M glutamate (15 min) and then maintained in DMEM for 24 hr in the absence of compound (Pre-treatment). Some cortical cultures were exposed to glutamate for 15 min, washed and maintained in DMEN for 24 hr in the presence of compund (Posttreatment). Cell viability was measured by the MTT assay. Optical density (OD) of the control and glutamate-treated were 1.18±0.09 and 0.75±0.07, respectively. Viability was calculated as the same as Table 1. Values given represent the mean SD (n=3). Mean value is significantly different from the value for the glutamate-treated $*p<0.05$, $**p<0.01$

TABLE 3

Effects of deoxyschizandrin, gomisin N and wuweizisu C on cell viability in NMDA- or KA-insulted primary cultured rat cortical cells.

|  | Viability (%) | |
|---|---|---|
|  | NMDA-insulted | KA-insulted |
| Control | 100.0 ± 1.4 | 100.0 ± 1.9 |
| NMDA or KA-treated | 0.0 ± 6.6 | 0.0 ± 5.6 |
| Deoxyschizandrin | 11.0 ± 3.5 | 38.2 ± 4.2* |
| Gomisin N | 45.5 ± 6.8** | 25.5 ± 4.5 |
| Wuweizisu C | 52.1 ± 7.1** | 15.0 ± 3.9 |

Rat cortical cultures were treated with compounds at the concentration of 1 M for 1 hr. The cultures were then exposed to 50 M NMDA or 50 M KA and were maintained for an additional 24 hr. glutamate and then maintained for 24 hr. Cell viability was measured by the MTT assay. Optical density of control, NMDA- and KA treated were 1.20±0.10, 0.77±0.05 and 0.85±0.08, respectively. Viability was calculated as the same as Table 1. Values given represent the mean SD (n=3). Mean value is significantly different from the value for the NMDA- or KA-treated; $*p<0.05$, $**p<0.01$

TABLE 4

Effects of deoxyschizandrin, gomisin N and wuweizisu C on intracellular Ca2+ ([Ca2+]i) in glutamate-damaged primary cultured rat cortical cells.

|  | [Ca2+]i (nM) | Protection (%) |
|---|---|---|
| Control | 85.6 ± 15.9 | 100.0 |
| Glutamate-treated | 419.0 ± 21.3 | 0.0 |
| Deoxyshizandrin | 350.7 ± 18.2 | 20.5 |
| Gomisin N | 218.0 ± 11.9*** | 60.3 |
| Wuweizisu C | 192.6 ± 9.1*** | 67.9 |

Rat cortical cultures were treated with compounds at the concentration of 1 M for 1 hr before exposure to 100 M glutamate and then maintained for 24 hr. Values given represent the mean SD (n=3). Mean value is significantly different from the value for the glutamate-treated; $***p<0.001$

TABLE 5

Effects of deoxyschizandrin, gomisin N and wuweizisu C on nitric oxide (NO) content in glutamate-damaged primary cultured rat cortical cells.

|  | Nitrate (nM) | Protection (%) |
|---|---|---|
| Control | 90.2 ± 3.7 | 100.0 |
| Glutamate-treated | 141.8 ± 5.7 | 0.0 |
| Deoxyschizandrin | 121.9 ± 3.1** | 40.2 |
| Gomisin N | 111.4 ± 3.3*** | 60.2 |
| Wuweizisu C | 107.6 ± 2.9*** | 65.8 |

Rat cortical cultures were treated with compounds at the concentration of 1 M for 1 hr before exposure to 100 M glutamate and then maintained for 24 hr. Values given represent the mean SD (n=3). Mean value is significantly different from the value for the glutamate-treated; ***p<0.001

TABLE 6

Effects of deoxyschizandrin, gomisin N and wuweizisu C on GSH-px activity in glutamate-injured primary cultured rat cortical cells.

|  | GSH-px ($\mu$mol NADPH consumed/min/mg protein) | Protection (%) |
|---|---|---|
| Control | 18.7 ± 2.7 | 100.0 |
| Glutamate-treated | 9.2 ± 3.3 | 0.0 |
| Deoxyschizandrin | 15.3 ± 3.0** | 62.1 |
| Gomisin N | 14.6 ± 4.1** | 56.8 |
| Wuweizisu C | 13.9 ± 3.9* | 49.5 |

Rat cortical cultures were treated with compounds at the concentration of 1 M for 1 hr before exposure to 100 M glutamate and then maintained for 24 hr. Values given represent the mean SD (n=3). Mean value is significantly different from the value for the glutamate-treated; *p<0.05, **p<0.01

TABLE 7

Effects of deoxyschizandrin, gomisin N and wuweizisu C on GSH content in glutamate-injured primary cultured rat cortical cells.

|  | GSH ($\mu$mol/mg protein) | Protection (%) |
|---|---|---|
| Control | 6.9 ± 1.7 | 100.0 |
| Glutamate-treated | 2.6 ± 0.7 | 0.0 |
| Deoxyschizandrin | 4.7 ± 1.1** | 48.8 |
| Gomisin N | 4.8 ± 1.3** | 51.2 |
| Wuweizisu C | 4.4 ± 0.9** | 41.9 |

Rat cortical cultures were treated with compounds at the concentration of 1 M for 1 hr before exposure to 100 M glutamate and then maintained for 24 hr. Values given represent the mean SD (n=3). Mean value is significantly different from the value for the glutamate-treated; **p<0.01

TABLE 8

Effects of deoxyschizandrin, gomisin N and wuweizisu C on MDA content in glutamate-injured primary cultured rat cortical cells.

|  | MDA (nmol/mg protein) | Protection (%) |
|---|---|---|
| Control | 70.2 ± 4.9 | 100.0 |
| Glutamate-treated | 198.2 ± 15.0 | 0.0 |
| Deoxyschizandrin | 135.4 ± 10.7** | 49.2 |
| Gomisin N | 125.6 ± 11.1*** | 57.0 |
| Wuweizisu C | 110.5 ± 9.0*** | 68.7 |

Rat cortical cultures were treated with compounds at the concentration of 1 M for 1 hr before exposure to 100 M glutamate and then maintained for 24 hr. Values given represent the mean SD (n=3). Mean value is significantly different from the value for the glutamate-treated;  p<0.01, * p<0.001

The present compound of general formula (I) can be administered 1 mg–200 mg/day, 1–3 times. That can be varied by weight, sex, age and severity of disease of a patient.

The compound of the general formula (I) of the present invention can be used for prevention and treatment of neurodegenerative disorders. The compound of the present invention can be formulated with conventional vehicle into pharmaceutical preparation such as injection, solution, syrup, tablet or capsule by a conventional method.

The present invention is more detailedly explained by the following preparation examples.

Preparation Example 1

| compound 1 | 10 mg |
|---|---|
| distilled water for injection | QS |
| pH adjuster | QS |

The compound 1 is dissolved in some distilled water for injection and the mixture is adjusted with pH adjuster to about pH 7.6. Distilled water for injection is poured to the mixture to make 2 ml and was filled in 2 ml ampoule.

Preparation Example 2

| compound 2 | 2 mg |
|---|---|
| distilled water for injectin | QS |
| pH adjuster |  |

The compound 2 is dissolved in some distilled water for injection and the mixture is adjusted with pH adjuster to about pH 7.6. Distilled water for injection is poured to the mixture to make 2 ml and was filled in 2 ml ampoule.

Preparation Example 3

| compound 3 | 10 mg |
|---|---|
| lactose | 100 mg |
| starch | 100 mg |
| magnesium stearate | QS |

The above ingredients are mixed and made into tablet by a conventional tablet method.

Preparation Example 4

| compound 1 | 10 mg |
|---|---|
| lactose | 100 mg |
| starch | 50 mg |
| magnesium stearate | QS |

The above ingredients are mixed and made into tablet by a conventional tablet method.

Preparation Example 5

| compound 2 | 5 mg |
|---|---|
| lactose | 50 mg |
| starch | 50 mg |
| talc | 2 mg |
| magnesium stearate | QS |

The above ingredients are mixed and filled in gelatine capsule by a conventional capsule method.

Preparation Example 6

| compound 1 | 5 mg |
|---|---|
| lactose | 100 mg |
| starch | 93 mg |
| talc | 2 mg |
| magnesium stearate | QS |

The above ingredients are mixed and filled in gelatine capsule by a conventional capsule method.

Preparation Example 7

| compound 3 | 50 mg |
|---|---|
| suger | 20 g |
| isomerized suger | 20 g |
| lemon essence | QS |
| distilled water | to make 100 ml |

The above ingredients are mixed and filled in 100 ml bottle and sterlized by a conventional solution method.

Preparation Example 8

| compound 1 | 50 mg |
|---|---|
| suger | 20 g |
| isomerized suger | 20 g |
| lemon essence | QS |
| distilled water | to make 100 ml |

The above ingredients are mixed and filled in 100ml bottle and sterilized by a conventional solution method.

Industrial Applicability

1. The compound of the general formula(I) significantly attenuated the neurotoxicity induced by L-glutamate in primary cultures of rat cortical cells.
2. The compound of the general formula (I) significantly lowered the $Ca^{2+}$ concentration excessive influx of $Ca^{2+}$ into neurons induced by glutamate.
3. The compound of the general formula (I) significantly increased the activity of glutathione peroxidase and the contents of glutathione induced by glutamateand supressed excess formation of NO induced by glutamate and supressed lipid-peroxidation.
4. From the above experimental results, the present compound of the general formula (I) can be used as pharmaceutical preparation for prevention and treatment of neurodegenerative disorders such as structural neurodegeneration caused by concussion of the brain and aging, 2nd phenomena like circulatory disorders, and for prevention and treatment of neurodegenerative disorders caused by various physical or mechanical factor like traffic accident, workman's accident, CO-poisoning.

What is claimed is:

1. A pharmaceutical preparation for treatment of neurodegenerative disorders comprising a compound of the general formula (I)

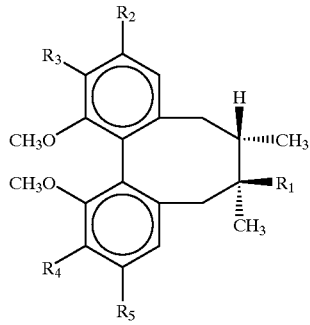

wherein $R_1$ is H or $C_{1-4}$ lower alkyl, $R_2$, $R_3$, $R_4$ and $R_5$ are respectively H, OH, $C_{1-4}$ lower alkyl, $C_{1-4}$ lower alkoxy, or $R_2$ and $R_3$ or $R_4$ and $R_5$ can be respectively combined to form the group of —$OCH_2O$— as active ingredient, in which the active ingredient is mixed with a conventional vehicle and formed into pharmaceutical preparation.

2. A method of treating a subject suffering from a neurodegenerative disease, comprising administering to the subject an effective amount of a compound of the following formula (I):

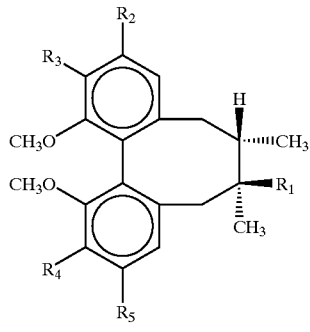

wherein $R_1$ is H or $C_{1-4}$ lower alkyl; $R_2$, $R_3$, $R_4$ and $R_5$ are respectively H, OH, lower alkyl, $C_{1-4}$ lower alkoxy, or $R_2$ and $R_3$ or $R_4$ and $R_5$ can be respectively combined to form the group —$OCH_2O$—.

3. The method of claim 2 wherein the subject is suffering from brain concussion.

4. The method of claim 2 wherein the subject is suffering from aging.

5. The method of claim 2 wherein the subject has suffered a stroke.

* * * * *